United States Patent [19]

Scheer

[11] Patent Number: 4,592,344

[45] Date of Patent: Jun. 3, 1986

[54] COMBINATION ILLUMINATOR AND LIP AND CHEEK EXPANDER

[76] Inventor: Peter M. Scheer, 420 Bond St., Redland, Calif. 92373

[21] Appl. No.: 561,586

[22] Filed: Dec. 14, 1983

Related U.S. Application Data

[63] Continuation of Ser. No. 335,202, Dec. 28, 1981, abandoned, which is a continuation-in-part of Ser. No. 172,257, Jul. 25, 1980, abandoned.

[51] Int. Cl.⁴ .............................................. A61B 1/06
[52] U.S. Cl. ........................................ 128/13; 433/29
[58] Field of Search ................................ 128/3, 10–18, 128/20, 76 R, 345; 433/29, 30; 362/32

[56] References Cited

U.S. PATENT DOCUMENTS

| | | | |
|---|---|---|---|
| 257,215 | 5/1882 | Doyle . | |
| 776,302 | 11/1904 | Crockett . | |
| 1,168,574 | 1/1916 | Spurr . | |
| 1,374,984 | 4/1921 | Cameron . | |
| 1,388,170 | 8/1921 | Cameron . | |
| 1,998,374 | 4/1935 | Lowry | 128/10 |
| 2,182,390 | 12/1939 | Reardon | 128/6 |
| 2,186,143 | 1/1940 | Neugass | 128/16 |
| 2,195,526 | 4/1940 | Traver | 240/2.18 |
| 2,201,331 | 5/1940 | Wright | 128/13 |
| 2,240,402 | 4/1941 | Joroslow | 88/39 |
| 2,247,258 | 6/1941 | Shepard | 128/18 |
| 2,539,828 | 1/1951 | Goldis et al. | 240/2.18 |
| 2,702,540 | 2/1955 | Debeh | 128/20 |
| 2,859,519 | 11/1958 | Cohn | 32/33 |
| 3,027,643 | 4/1962 | Cohen | 32/33 |
| 3,048,924 | 8/1962 | Whitman et al. | 433/30 |
| 3,195,536 | 7/1965 | Hovnanian et al. | 128/6 |
| 3,241,550 | 3/1966 | Gelarie | 128/12 |
| 3,397,457 | 8/1968 | Gosselin | 32/27 |
| 3,455,024 | 7/1969 | Gelarie | 32/33 |
| 3,590,232 | 6/1971 | Sadowski | 240/2 |
| 3,614,414 | 10/1971 | Gores | 240/2 |
| 3,614,415 | 10/1971 | Edelman | 240/2.18 |
| 3,616,792 | 11/1971 | Pleet | 128/11 |
| 3,634,938 | 1/1972 | Hutchinson | 32/27 |
| 3,638,013 | 1/1972 | Keller | 240/41.15 |
| 3,758,951 | 9/1973 | Scrivo et al. | 32/27 |
| 3,789,835 | 2/1974 | Whitman | 128/18 |
| 3,851,642 | 12/1974 | McDonald | 128/18 |
| 3,916,879 | 11/1975 | Cotten | 128/12 |
| 3,916,880 | 11/1975 | Schroer | 128/12 |
| 3,938,508 | 2/1976 | Buckner | 128/76 |
| 3,986,854 | 10/1976 | Scrivo et al. | 65/4 |
| 4,002,162 | 1/1977 | Weisser | 128/17 |
| 4,019,255 | 4/1977 | Cohen et al. | 32/33 |
| 4,156,424 | 5/1979 | Burgin | 128/18 |
| 4,171,572 | 10/1979 | Nash | 32/27 |
| 4,200,089 | 4/1980 | Inoue | 128/12 |
| 4,233,649 | 11/1980 | Scheer et al. | 362/32 |
| 4,263,899 | 4/1981 | Burgin | 128/18 |

FOREIGN PATENT DOCUMENTS

674647 1/1930 France .

Primary Examiner—Edward M. Coven
Assistant Examiner—Max F. Hindenburg
Attorney, Agent, or Firm—Price, Heneveld, Huizenga & Cooper

[57] ABSTRACT

An illuminating lip and cheek expanding device comprising a lip expander including a pair of lip engaging members to engage opposite corners of the mouth. At least one of the lip engaging members includes a fiber optic bundle having a light outlet end located at the periphery of the mouth and facing inwardly toward the teeth of the mouth to be illuminated. The fiber optic bundle also has a light inlet end connected to the light outlet end and adapted to be connected to a light source, so that light from said source may be conveyed through said fiber optic bundle and onto the teeth.

14 Claims, 12 Drawing Figures

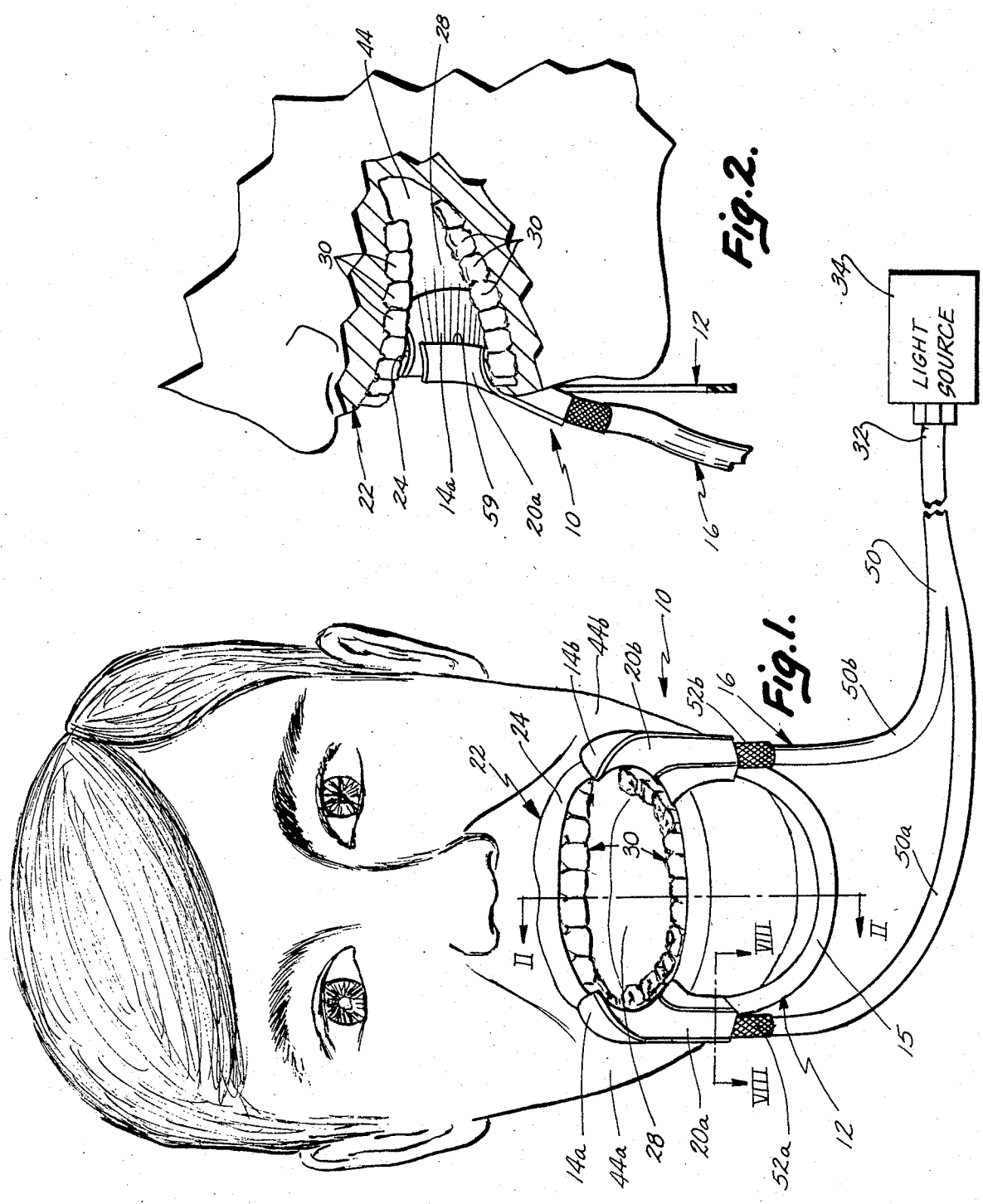

COMBINATION ILLUMINATOR AND LIP AND CHEEK EXPANDER

This is a continuation of application Ser. No. 335,202, filed Dec. 28, 1981, now abandoned which is a continuation-in-part of application Ser. No. 172,257, filed July 25, 1980, now abandoned.

BACKGROUND OF THE INVENTION

The present invention relates to illuminating devices and more particularly for devices used to illuminate a dental patient's mouth for examination and/or operative purposes.

It is very difficult to properly illuminate the interior of a dental patient's mouth due to the fact that (1) the oral cavity must be illuminated through a relatively restricted opening (i.e. the lips) and (2) the dentist must work in close proximity to the mouth, thus normally blocking light from entering the oral cavity. However, proper illumination is absolutely essential for the many delicate operations and procedures for dental treatment and oral surgery. Previous oral illumination devices are unsatisfactory.

Most typically, the oral cavity is illuminated using a focused light mounted approximately two to three feet above the dental chair and arranged to direct light onto and into the mouth. The amount of light entering the oral cavity using such an arrangement is somewhat limited due to the fact that the light source is remote from the patient's mouth. Additionally, the dentist or oral surgeon must often position himself between the light and the patient to properly view the mouth and, accordingly, blocks light from entering the mouth.

It is also well known to incorporate illumination means, particularly fiber optic illumination means, on handheld dental instruments. Typically, one or two fiber optic strands extend longitudinally of the instrument and have a light outlet end arranged to direct light at the action end of the instrument in "headlight" fashion. However, such an arrangement directs light only on a limited area and does not provide illumination for the entire oral cavity. Additionally, the presence of the illumination means, typically as an add-on feature, on the instrument interferes with the comfortable and proper use of the instrument.

Although several devices have been specifically designed for illuminating an interior portion of the oral cavity, these devices typically extend far into the cavity, interfering with the proper movement of the many treatment and surgical instruments required for examination and/or operative treatment. (see U.S. Pat. No. 3,616,792 entitled ILLUMINATING SURGICAL SPECULA and issued Nov. 2, 1971, to Pleet; U.S. Pat. No. 1,998,374 entitled DENTAL SPECULUM and issued Apr. 16, 1935, to Lowry; and French Pat. No. 674,647.) Additionally, these devices do not adequately illuminate the teeth and surrounding area.

Although a wide variety of lip and cheek expanders, and other mouth spreaders, have been developed, these devices typically do not include illumination means to effect proper lighting of the oral cavity, particularly the teeth and surrounding area.

SUMMARY OF THE INVENTION

The aforementioned problems are solved by the present invention wherein a combination illuminator and lip and cheek expander is provided including an illumination means located at the periphery of the oral cavity on lip expanders engaging the corners of the patient's mouth. Neither the expander, nor the illumination means mounted thereon, penetrates any further than the immediate lip region so that the interior of the oral cavity immediately adjacent the lip periphery and inwardly thereof is properly illuminated without the device interfering with the movement of instruments within the cavity. Further, while illuminating the oral cavity, the present device engages the opposite corners of the mouth to expand both the lips and cheeks and thus assist in holding the patient's mouth in an open position. The present device not only does not interfere with the insertion of other instruments into the patient's mouth, but actually enlarges the opening through which instruments must be inserted.

More particularly, the present device comprises a lip expander including a pair of lip engaging members to engage opposite corners of a mouth to spread the lips and cheeks and hold the mouth in an open position. At least one of the lip engaging members includes inwardly facing fiber optic light transmitting means having light outlet means located in the plane of the lips at the periphery of the mouth. A light inlet means is connected to the light outlet means and adapted to be connected to a light source to convey light from the source to the light outlet means and into the patient's mouth.

These and other objects, advantages, and features of the invention will be more fully understood and appreciated by reference to the written specification and the appended drawings.

BRIEF DESCRIPTION OF THE DRAWINGS

FIG. 1 is a fragmentary, elevational view of the combination illuminator and lip and cheek expander of the present invention mounted in a patient's mouth;

FIG. 2 is a partially sectional view taken along plane II—II in FIG. 1;

DESCRIPTION OF THE PREFERRED EMBODIMENT

Figure 3:
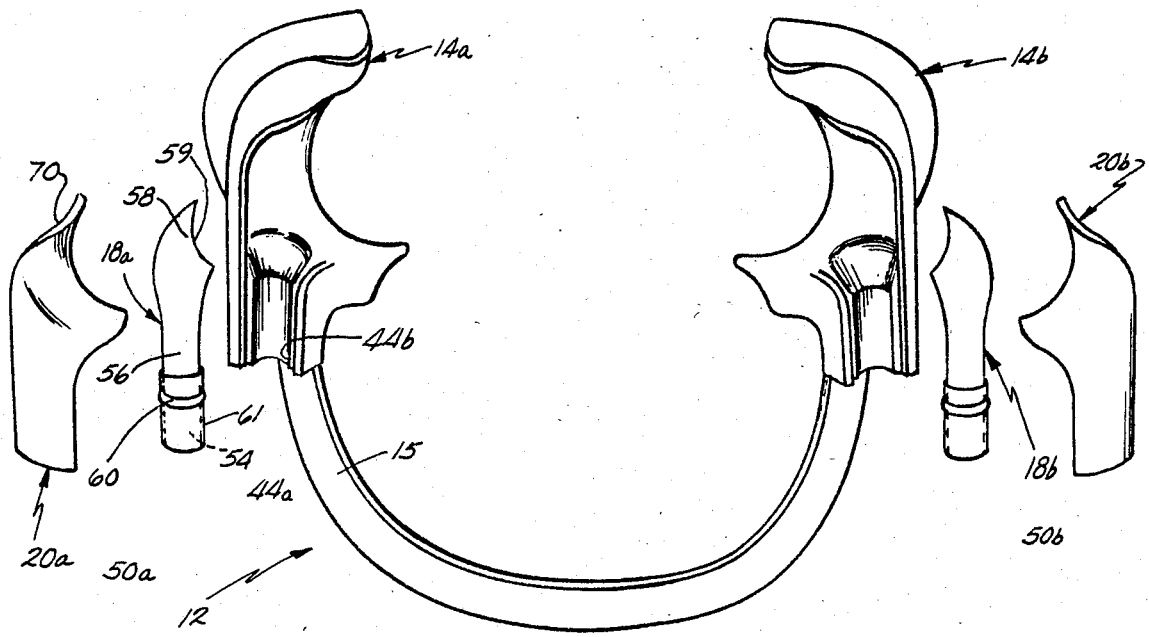
FIG. 3 is an exploded view of the lip and cheek expander.

A combination illuminator and lip and cheek expander 10 (FIG. 1) constructed in accordance with a preferred embodiment of the invention comprises lip and cheek expander 12, including a pair of opposed lip engaging members 14a and 14b, fiber optic assembly 16, including outlet pieces 18a and 18b mounted on members 14a and 14b, respectively, and covers 20a and 20b securing the outlet pieces in place on the expander. Device 10 is mounted within mouth 22 (FIGS. 1 and 2), and more particularly on the corners of the upper and lower lips 24 and 26, to illuminate oral cavity 28 including teeth 30. Fiber optic assembly 16 includes light inlet end 32, which is adapted to be connected to light source 34 to convey light from the source through assembly 16 and into cavity 28.

Lip and cheek expander 12 (FIG. 3) includes two lip engaging members 14a and 14b flexingly joined by connecting bar 15. Preferably, expander 12 is integrally molded of a resilient, plastic material so that bar 15, when flexed, resiliently urges members 14a and 14b away from one another. Further, the material of which expander 12 is fabricated should be capable of withstanding relatively high temperatures so that the expander may be autoclaved.

Figure 5:
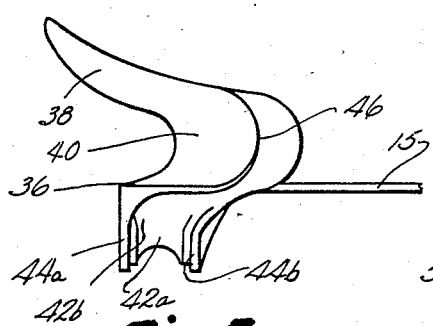
FIG. 5 is a fragmentary, top plan view of the lip engaging member shown in FIG. 4.

Lip engaging members 14a and 14b are generally identical to one another with the exception that member 14b is the mirror image of member 14a. Accordingly, only member 14a will be described in detail, with the description of member 14b being the logical, equivalent extension thereof. Member 14a (FIGS. 4, 5, and 6) generally includes outer U-shaped flange 36, inner U-shaped flange 38, and intermediate bite portion 40 interconnecting the outer flange 36 and the inner flange 38. Molded integrally with the outer flange 36 is a light outlet receiving extension 37 having a channel 42 comprising the semi-cylindrical portion 42a, flared portion 42b, and fan-shaped portion 42c. Extension 37 also defines opposed grooves 44a and 44b extending the full length of channel 42 (FIGS. 4 and 8) which receive the ribs 66a and 66b, respectively, to said in centering cover 20a on extension 37 and flange 36.

Inner flange 38 is a U-shaped arcuate member designed to comfortably fit against the interior of the lips and cheek to draw the cheek away from the teeth when expander 12 is in position in the mouth. The interior surface of flange 38 may be covered with a reflective coating to improve illumination of the mouth. Intermediate bite portion 40 is generally arcuate in shape, being concave outwardly, and includes upper portion 46 and lower portion 48, which engage the upper and lower lips, respectively.

Fiber optic assembly 16 includes a sheathed fiber optic bundle 50 (FIGS. 1 and 2) and light outlet pieces 18a and 18b (FIG. 3). Bundle 50 (FIG. 1) is well-known to those skilled in the art and includes light inlet end 32 adapted to be connected to light source 34. Proximate expander 12, bundle 50 separates into two branches 50a and 50b leading to outlet pieces 18a and 18b, respectively. Branches 50a and 50b terminate in knurled push-fit couplings 52a and 52b, respectively, which may be readily installed on, and removed from, outlet pieces 18a and 18b.

Figure 6:
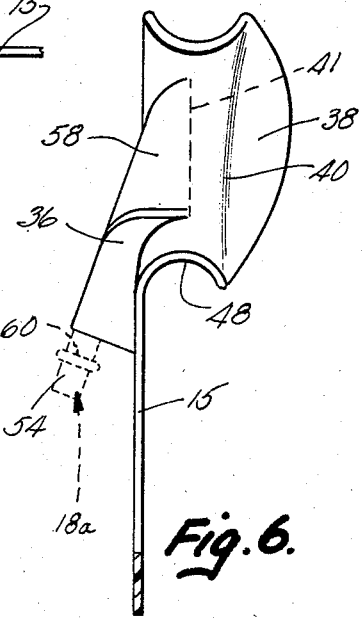
FIG. 6 is a fragmentary, side elevational view of the lip engaging member shown in FIG. 4 with the light outlet piece and cover removed but with the light outlet piece being shown in phantom.

Light outlet pieces 18a and 18b (FIG. 3) are generally identical to one another with the exception that piece 18b is the mirror image of piece 18a. Accordingly, only piece 18a will be described in detail, with the description of piece 18b being the logical, equivalent extension thereof. Piece 18a includes a generally cylindrical lower shaft portion 54, an intermediate flaring portion 56 extending upwardly therefrom, and an upper fan-shaped portion 58 extending from the flaring portion opposite the shaft. Fanshaped portion 58 flares out from the compact, cylindrical shape of bundle 50 and shaft 54 to effect broader illumination of the oral cavity. Portion 58 terminates in edge 59 positioned along lip intermediate bite portion 40 in the assembled expander (see FIG. 2). When assembled, shaft portion 54 fits within the semi-cylindrical channel portion 42a of channel 42, flared portion 56 within flared portion 42b, and fan-shaped portion 58 in fan-shaped portion 42c. Terminal edge 59 of fan-shaped portion 58 is located at the line 41 of the intermediate portion 40, (FIG. 6). Piece 18a is fabricated from well-known fiber optic components, preferably a plurality of fiber optic strands. The bundled strands have a generally compact, circular cross section at shaft 54 and are spread out, or arranged, into a fan shape at end portion 58. Each strand of a given cross section conveys or transmits approximately the same amount of light as another strand having a similarly sized cross section. Consequently, piece 18a provides generally uniform distribution along the length of edge 59. Preferably metal sheath 61 is secured about shaft 54 and supports resilient O-ring 60, which aids in the securement of push-fit coupling 52a and shaft 54.

Figure 8:
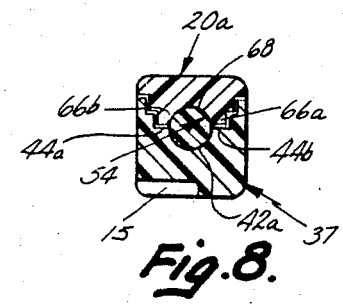
FIG. 8 is a sectional view taken along plane VIII—VIII in FIG. 1.
Figure 4:
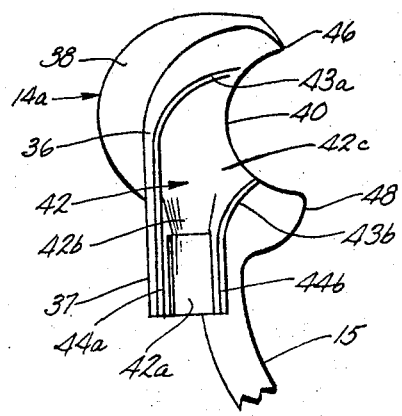
FIG. 4 is a fragmentary, front elevational view of a lip engaging member.
Figure 7:
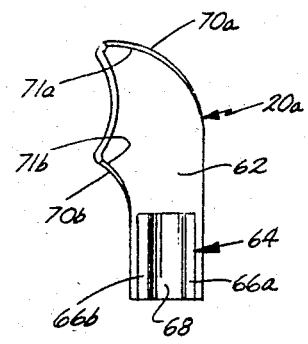
FIG. 7 is a rear, elevational view of the cover which fits over the light outlet piece on the lip engaging member of FIG. 6.

Covers 20a and 20b (FIGS. 3 and 7) are generally identical to one another with the exeption that cover 20b is the mirror image of cover 20a. Accordingly, only cover 20a will be described in detail, with the description of cover 20b being the logical, equivalent extension thereof. Cover 20a includes a top portion 61 having an inside surface 62 which is curvilinearly shaped to closely overlay portions 56 and 58 of outlet piece 18a. Projection 64 extends from portion 61 and defines semi-cylindrical channel 68 and ribs 66a and 66b for receiving grooves 44a and 44b of extension 37 (FIGS. 4, 7, and 8). Cover 62 terminates in its opposite sides 70a and 70b in ribs 71a and 71b, respectively, which extend from the edges of rear surface 62 to engage grooves 43 in the surfaces of the outer flange 36 and extension 37.

Assembly and Operation

Assembly of device 10 begins by positioning outlet piece 18a within channel 42 on lip engaging member 14a. Shaft portion 54 is located in semi-cylindrical portion 42a, flared portion 56 in flared portion 42b, and fan-shaped portion 58 in fan-shaped portion 42c. When outlet piece 18a is properly positioned, terminal edge 59 is located on portion 40 at line 41 (FIG. 6) intermediate upper and lower portions 46 and 48 and also intermediate inner flange 38 and outer flange 36. Further, edge 59 faces inwardly toward those portions of the mouth to be illuminated. Cover 20a is then positioned over outlet piece 18a with ridges or ribs 66a and 66b located in grooves 44a and 44b, respectively, and channel 68 receiving shaft portion 54 (FIG. 8). When properly positioned, rear surface 62 lies over fan-shaped end 58 and ridges or ribs 71a and 71b engage the surfaces of outer flange 36 and extension 37 along their entire lengths. Cover 20a is then secured to lip engaging member 14a, using epoxy adhesive, or any other suitable fastening means. To complete assembly, outlet piece 18b and cover 20b are secured to lip engaging member 14b in an analogous manner.

When device 10 is to be used to illuminate mouth 22 (FIGS. 1 and 2), fiber optic bundle 50, and more particularly branches 50a and 50b are connected to outlet pieces 18a and 18b, respectively, by securing push-fit connections 52a and 52b over shafts 54 and O-rings 60. Lip engaging members 14a and 14b are flexed toward one another by flexing the connecting bar 15; and inner flanges 38 are then tucked into patient's mouth 22 so that members 14a and 14b engage opposite corners of the mouth. Device 10 is then released so that lip engaging members 14a and 14b are biased away from one another by connecting bar 15 and into engagement with the opposite corners of the mouth. Inner flanges 38 engage the inside of lips 24 and 26 of cheeks 44 to pull the cheeks away from teeth 30. Intermediate portions 40 engage the opposite corners of mouth 22 to spread lips 24 and cheeks 44 as well as holding the mouth open. Upper and lower lips 24 and 26 are engaged by upper and lower portions 46 and 48 of each lip engaging member 14a and 14b to force the lips apart. Outer flanges 36 engage the exterior surfaces of lips 24 and 26 to said in positioning device 10.

End 32 of bundle 50 is then connected to light source 34, and the light source is actuated to introduce light into the bundle. Light is transmitted through bundle 50 and branches 50a and 50b to outlet pieces 18a and 18b. Terminal edges 59 of fan-shaped portions 58 are located so as to be generally coplanar with lips 24 and 26. Consequently, device 10 through outlet pieces 18a and 18b illuminates the entire oral cavity 28 inwardly from lips 24 and 26. Further, because of the fan-shape of portion 58, light is evenly distributed over a broader area than would be possible if the optic bundle 50 merely terminated in its compact, cylindrical shape.

Alternative Embodiments

Figure 10:
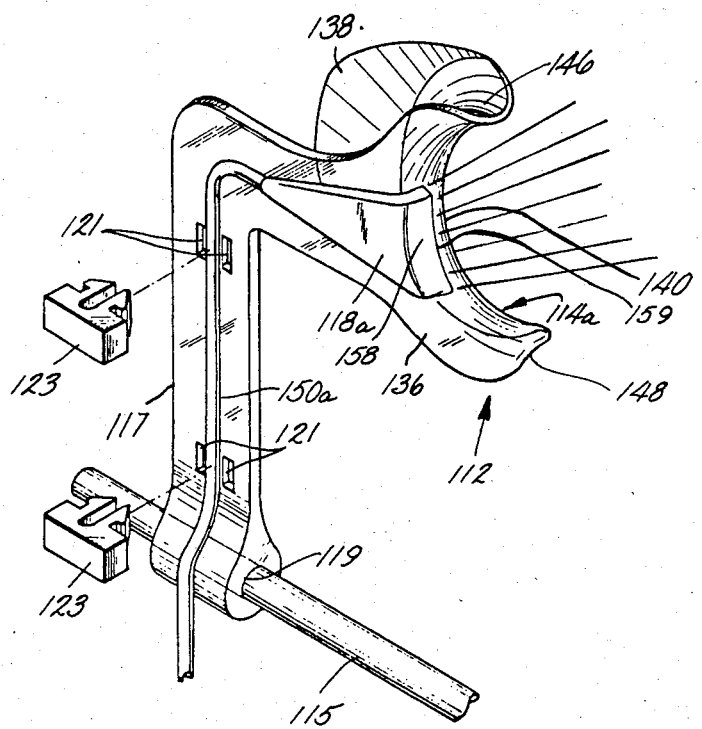
FIG. 10 is a fragmentary, perspective view of the alternative embodiment illuminator and expander shown in FIG. 8.
Figure 11:
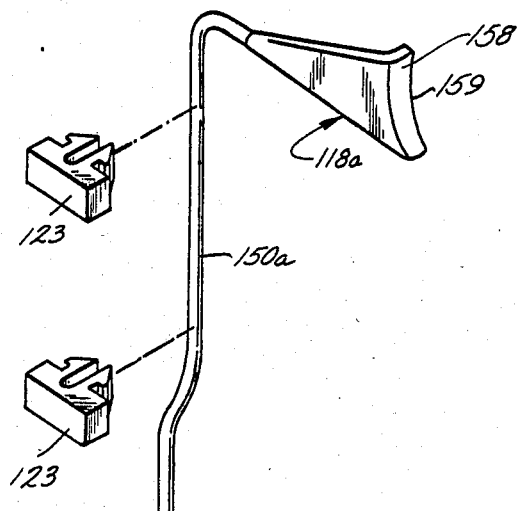
FIG. 11 is a fragmentary, perspective view of the light conveying structure and clips shown in FIGS. 9 and 10.

Alternative device 110 (FIGS. 9, 10, and 11) includes lip engaging members 114a and 114b slidably mounted on a common connecting bar 115. Fiber optic assembly 116 is mounted on lip engaging members 114a and 114b to provide illumination for oral cavity 128.

Members 114a and 114b are generally indentical to one another with the exception that member 114b is the mirror image of member 114a. Consequently, only member 114a will be described in detail with the description of member 114b being the logical equivalent thereof. Member 114a (FIG. 10) includes a downwardly depending arm 117 defining two pairs of clip apertures 121 and bore 119 at its lower end through which bar 115 passes. It further includes outer flange 136, integrally connected to arm 117, interior flange 138, and intermediate portion 140 including upper and lower portions 146 and 148 and interconnecting the outer flange 136 and the interior flange 138. Flanges 136, 138, and portion 140 are shaped similarly to their counterparts in embodiment 10, and consequently a detailed description is unnecessary.

Figure 9:
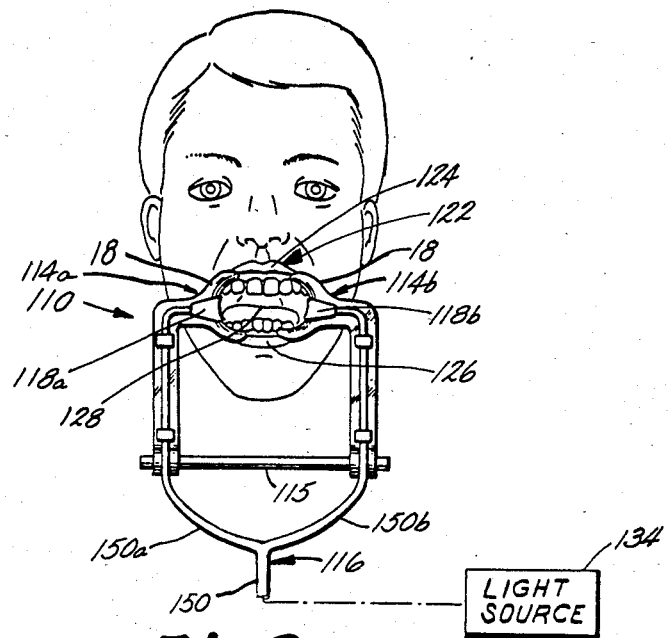
FIG. 9 is an elevational view of an alternative embodiment of the combination illuminator and lip and cheek expander mounted in a patient's mouth.

Optic assembly 116 includes branch bundle 150a (FIGS. 10 and 11) mounted on arm 117, and outlet piece 118a mounted on outer portion 136 and intermediate portion 140. Branch 150a is placed adjacent arm 117 and between pairs of clip apertures 121 so that spring clips 123 may be inserted into the arm through the clip apertures securing the branch in place. Outlet piece 118a is secured in position, preferably using epoxy glue or any other suitable adhesive, and arranged so that terminal edge 159 of flared end 158 is located intermediate inner and outer flanges 136 and 138 and intermediate upper and lower portions 146 and 148. Both of bundle branches 150a and 150b are connected through bundle 150 to light source 134 (FIG. 9).

The operation of alternative device 110 is generally similar to that of device 10, and accordingly a detailed description is unnecessary. Suffice it to say that lip engaging members 114a and 114b are slid toward one another along bar 115 so that inner flanges 138 may be tucked underneath upper and lower lips 124 and 126 at opposite corners of mouth 122. Lip engaging members 114a and 114b are then urged outwardly along bar 115, expanding the patient's lips and cheeks and holding the patient's mouth in an open position. Because terminal edge 159 of outlet pieces 118a and 118b are generally coplanar with lips 124 and 126, alternative device 110 illuminates oral cavity 128 including the area immediately inside lips 124 and 126.

Figure 12:
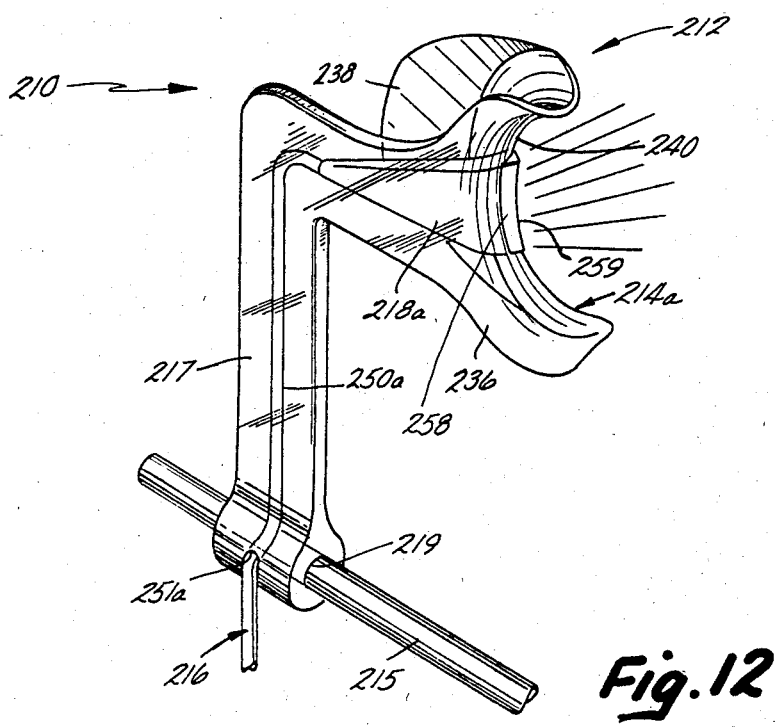
FIG. 12 is a fragmentary, perspective view of another alternative embodiment of the combination illuminator and lip and cheek expander.

Arm 214a of another alternative device 210 is shown in FIG. 12. The primary difference between device 210 and device 110 is that optic assembly 216 is partially embedded within the lip engaging members. Lip engaging member 214a is generally identical to member 114a, with the exception that member 214 does not include clip apertures. Bundle branch 250a enters arm 217 through aperture 251a. That portion of branch 250a between aperture 251a and outlet piece 218a is totally encapsulated within the arm. Outlet piece 218a is also partially encapsulated within outer portion 236 so that only terminal edge 259 of flared portion 258 extends out of intermediate portion 240.

The operation of device 210 is generally similar to that of device 110, and accordingly a detailed description is unnecessary. Suffice it to say that lip engaging members 214a and 214b are positioned within the patient's mouth to spread the lips and cheeks and hold the mouth in an open position. Optic assembly 216 transmits light from a light source to terminal edge 259 of outlet piece 218a to distribute light evenly throughout the oral cavity. The fan shape of portion 258 provides a light distribution over a broader area than if outlet piece 218a terminated in a compact shape.

It should be understood that the above description is intended to be that of preferred embodiments of the invention. Various changes and alterations might be made without departing from the spirit and broader aspects of the invention as set forth in the appended claims, which are to be interpreted in accordance with the principles of patent law, including the doctrine of equivalents.

The embodiments of the invention in which an exclusive property or privilege is claimed are defined as follows:

1. A lip and cheek expanding device for holding a mouth in an open position and for conveying light from a source to the interior of the mouth around the teeth for illumination purposes comprising:
   a lip expander for spreading the mouth and cheeks, said lip expander including a pair of lip engaging members of arcuate configuration, each having an inner surface with upper and lower portions shaped to engage portions of the upper and lower lips of the mouth, each having an outer surface portion in the shape of an arc facing the outer surface portion of the other, said lip expander further including means for connecting and positioning said lip engaging members one from the other to engage opposite corners of the mouth, said positioning means located outside of the mouth when said expanding device holds the mouth in the open position; and each of said lip engaging members including a fiber optic light transmitting means having light outlet means located on the arc of said outer surface portion and intermediate said upper and lower portions; said fibers of light outlet means being arranged so as to be fanned and flattened out and arcuately shaped to extend a distance along said arc to produce an exposed fiber outlet edge extending a distance along said arc and facing inwardly toward those portions of the mouth around the teeth for projecting light over a broad area of the teeth illuminating the portions to be examined and/or operated on when said lip and cheek expanding device holds the mouth in the open position; and light inlet means for connecting said light outlet to a light source whereby when said light outlet means is operatively connected to the light source the portions of the mouth are illuminated by light transmitted from the light source through said light transmitting means.

2. An expanding device as defined in claim 1 wherein said light transmitting means has substantially a cylindrical cross section between said light inlet means and said light outlet means, and wherein said light outlet means is spread out along said arc from said cylindrical cross section to a fan-shaped cross section at said edge, the width of said fan-shaped edge extending along said arc in a direction between said upper and lower portions for effecting a distribution of light over a broader area along said teeth.

3. An expanding device as defined in claim 1 wherein said one lip engaging member defines a channel in which a portion of said light transmitting means is positioned, and further comprising a cover secured over said channel entrapping and securing said light transmitting means in position.

4. An expanding device as defined in claim 1 wherein said light outlet means is embedded within said one lip engaging member.

5. An expanding device as defined in claim 1 wherein said light transmitting means is removably mounted on said lip expander.

6. An expanding device as defined in claim 1, 2, 3, 4 or 5 wherein said light transmitting means comprise fiber optic light transmitting means.

7. An expanding device as recited in claim 1, 4 or 5 further comprising a reflective surface on a portion of said one lip engaging member facing the interior of the mouth to improve illumination of the mouth.

8. A lip and cheek expanding device for holding a mouth in an open position and for conveying light from a source to the interior of the mouth around the teeth for illumination purposes comprising:

a lip expander for spreading the mouth and cheeks, said lip expander including a pair of lip engaging members of arcuate configuration, each having upper and lower portions shaped to engage portions of the upper and lower lips of the mouth, each having interior and exterior portions shaped to engage interior and exterior portions of the lips; said exterior portions including an outer surface in the shape of an arc said lip expander further including means for connecting and positioning said lip engaging members one from the other to engage opposite corners of the mouth, said positioning means located outside of the mouth when said expanding device holds the mouth in the open position; and each of said lip engaging members including fiber optic light transmitting means having light outlet means with an exposed fiber optic outlet edge thereof located on the arc of said outer portions intermediate said upper and lower portions and a portion extending from said exposed outlet edge intermediate said interior and exterior portions, said exposed fiber optic outlet edge of said light outlet means being arranged so as to be fanned and flattened out and shaped to extend a distance along said arc to produce said edge and facing inwardly toward those portions of the mouth around the teeth for projecting light over a broad area for illuminating the portions to be examined and/or operated on when said lip and cheek expanding device holds the mouth in the open position; and said fiber optic light transmitting means including light inlet means for operatively connecting said light outlet means to a light source whereby, when said light outlet means is operatively connected to the light source, the portions of the mouth are illuminated by light transmitted from the light source through said light transmitting means.

9. An expanding device as defined in claim 1 wherein said light transmitting means has substantially a cylindrical cross section being fanned out and shaped to extend a distance along said arc and for effecting a distribution of light over a broader area along said teeth.

10. An expanding device as defined in claim 8 wherein said one lip engaging member defines a channel in which a portion of said light transmitting means is positioned and further comprising a cover secured over said channel entrapping and securing said light transmitting means in position.

11. An expanding device as defined in claim 8 wherein said light outlet means is embedded within said one lip engaging member.

12. An expanding device as defined in claim 8 wherein said light transmitting means is removably mounted on said lip expander.

13. An expanding device as defined in claim 8, 9, 10, 11 or 12 wherein said light transmitting means comprise fiber optic light transmitting means.

14. An expanding device as recited in claim 8, 11, or 12 further comprising a reflective surface on a portion of said one lip engaging member facing the interior of the mouth to improve illumination of the mouth.

* * * * *